US012635896B2

(12) United States Patent
Ng

(10) Patent No.: US 12,635,896 B2
(45) Date of Patent: May 26, 2026

(54) BIO-IMPEDANCE MEASUREMENT DEVICE AND BIO-IMPEDANCE MEASUREMENT METHOD

(71) Applicant: Serial microelectronics information limited, Taipei City (TW)

(72) Inventor: Si Herng Ng, Hsinchu County (TW)

(73) Assignee: Serial microelectronics information limited, Taipei City (TW)

( * ) Notice: Subject to any disclaimer, the term of this patent is extended or adjusted under 35 U.S.C. 154(b) by 261 days.

(21) Appl. No.: 18/631,019

(22) Filed: Apr. 9, 2024

(65) Prior Publication Data

US 2025/0311938 A1 Oct. 9, 2025

(51) Int. Cl.
*A61B 5/053* (2021.01)
(52) U.S. Cl.
CPC .................................... *A61B 5/053* (2013.01)
(58) Field of Classification Search
CPC .............................. A61B 5/053; A61B 5/0531
See application file for complete search history.

(56) References Cited

U.S. PATENT DOCUMENTS

| | | | | |
|---|---|---|---|---|
| 9,853,611 B2 * | 12/2017 | Chang | ........................ | H03F 1/34 |
| 2004/0158167 A1 * | 8/2004 | Smith | .................... | A61B 5/053 |
| | | | | 600/547 |
| 2005/0151545 A1 * | 7/2005 | Park | ........................ | G01R 27/02 |
| | | | | 324/679 |

* cited by examiner

*Primary Examiner* — Eric F Winakur
(74) *Attorney, Agent, or Firm* — Winston Hsu

(57) ABSTRACT

A bio-impedance measurement device, for measuring a bio-impedance, includes an electrode; a negative capacitance circuit, coupled to the electrode; a signal generator, configured to input a probing signal into the negative capacitance circuit; a demodulation circuit, coupled to the electrode and the negative capacitance circuit, configured to receive a first response signal related to the probing signal from the negative capacitance circuit and generate a first in-phase signal and a first quadrature-phase signal according to the first response signal, wherein the demodulation circuit and the electrode comprise an input capacitance; and a processor, coupled to the negative capacitance circuit and the demodulation circuit, configured to adjust the negative capacitance circuit to cancel the input capacitance according to the first in-phase signal and the first quadrature-phase signal.

8 Claims, 12 Drawing Sheets

FIG. 6

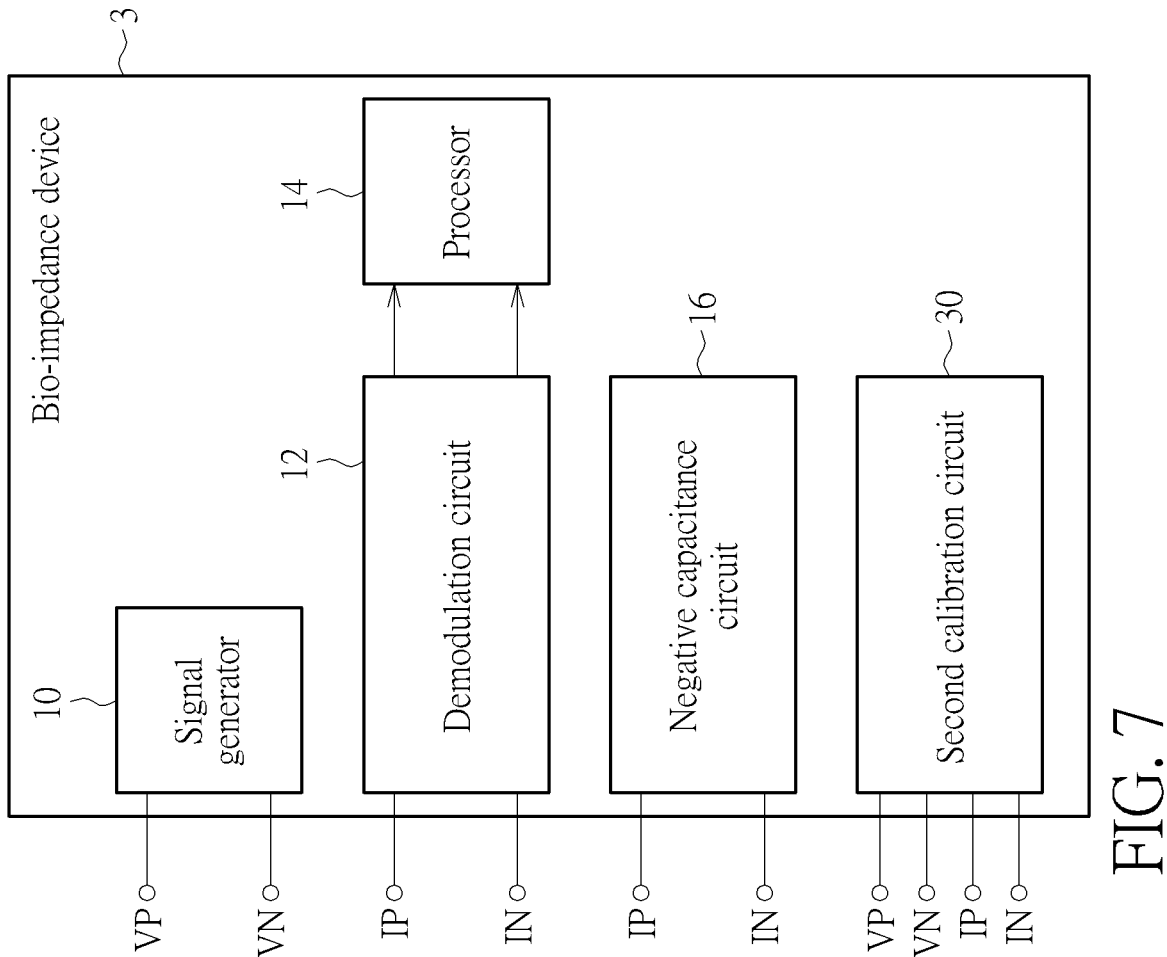
FIG. 7
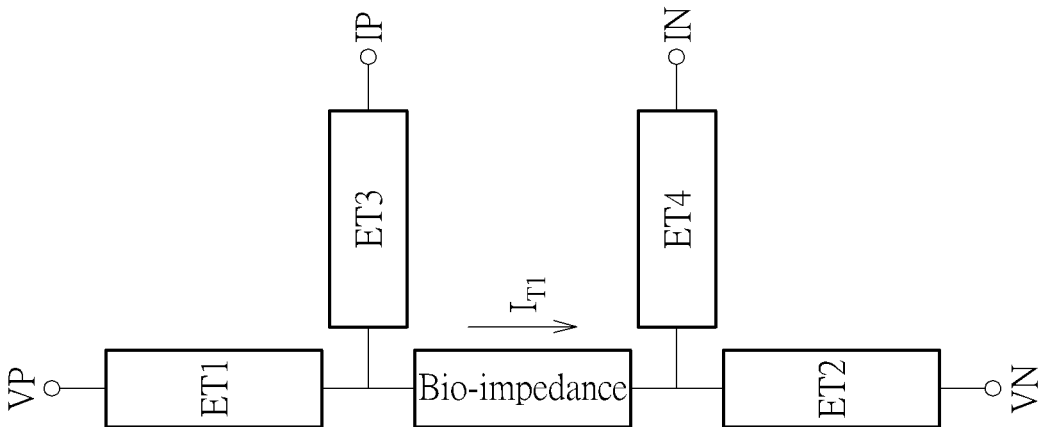

S900
Start

Disconnect the bio-impedance from the electrodes ET1, ET2, ET3, ET4   S902

Generate a reference phase   S904

Generate a calibration phase   S906

Adjust the negative capacitance circuit 16 to cancel the parasitic capacitance $C_{IP}$, $C_{IN}$ according to the reference phase and the calibration phase   S908

S910
End

1

BIO-IMPEDANCE MEASUREMENT DEVICE AND BIO-IMPEDANCE MEASUREMENT METHOD

BACKGROUND OF THE INVENTION

1. Field of the Invention

The present invention relates to a bio-impedance measurement device and a bio-impedance measurement method, and more particularly, to a bio-impedance measurement device and a bio-impedance measurement method that utilize a negative capacitance circuit to cancel an input capacitance of an electrode.

2. Description of the Prior Art

A bio-impedance measurement device is used to gauge the impedance of a user's body at a specific frequency. The bio-impedance measurement device introduces a probing signal into the user's body, measures a response signal related to the probing signal, computes the impedance value based on the response signal, and analyzes the impedance value to determine body compositions such as body fat and muscle mass. However, electrodes used by the bio-impedance measurement device to connect to the user's body have the parasitic capacitor and the parasitic resistor. In such a circumstance, part of the probing signal may be coupled to the parasitic capacitor, which means that the probing signal is not completely introduced into the user's body, causing errors in the body compositions obtained by the bio-impedance measurement device analyzing the response signal. Therefore, how to reduce the impact of the input capacitor of the electrodes has become one of the goals in the industry.

SUMMARY OF THE INVENTION

Therefore, the purpose of the present invention is to provide a bio-impedance measurement device and a bio-impedance measurement method to improve the drawback of the prior art.

The embodiment of the present invention discloses bio-impedance measurement device, comprising a signal generator, configured to input a probing signal having a first frequency and an over-sampling pattern into a bio-impedance; a receiver, configured to receive a first response signal related to the probing signal from the bio-impedance; a demodulation circuit, coupled to the receiver, configured to generate a first in-phase signal and a first quadrature-phase signal according to the first response signal; and a processor, coupled to the signal generator and the demodulation circuit, configured to analyze the probing signal, the first in-phase signal and the first quadrature-phase signal to determine a bio-impedance value of the bio-impedance.

The embodiment of the present invention discloses a bio-impedance measurement method, for a bio-impedance measurement device, comprising inputting, by a signal generator of the bio-impedance measurement device, a probing signal into a negative capacitance circuit of the bio-impedance measurement device; receiving, by a demodulation circuit of the bio-impedance measurement device, a first response signal related to the probing signal from the negative capacitance circuit; generating, by the demodulation circuit, a first in-phase signal and a first quadrature-phase signal according to the first response signal; and analyzing, by a processor of the bio-impedance measurement device, the probing signal, the first in-phase signal and the first quadrature-phase signal to adjust the negative capacitance circuit to cancel an input capacitance between the demodulation circuit and an electrode of the bio-impedance measurement device.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 6 is a schematic diagram of a bio-impedance measurement system according to another embodiment of the present invention.

FIG. 7 is a schematic diagram of a bio-impedance measurement device according to an embodiment of the present invention.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to". Also, the term "couple" is intended to mean either an indirect or direct electrical connection. Accordingly, if one device is coupled to another device, that connection may be through a direct electrical connection, or through an indirect electrical connection via other devices and connections.

Figure 1:
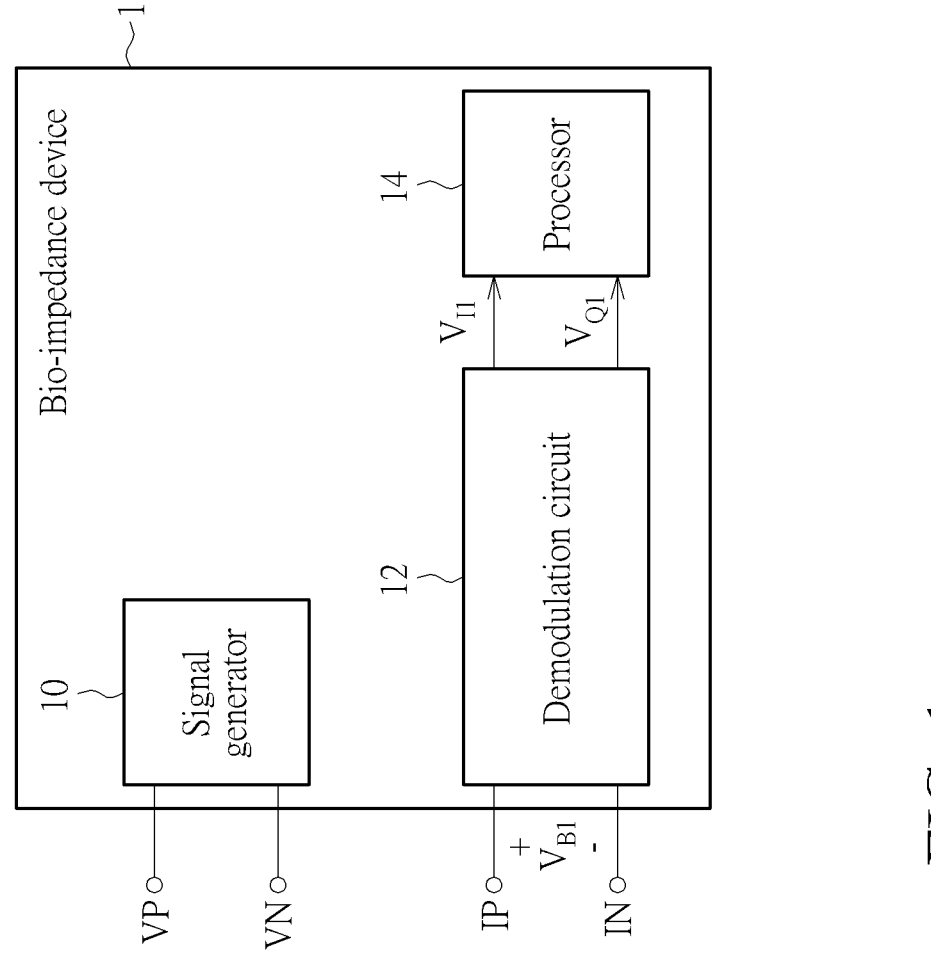
FIG. 1 is a schematic diagram illustrating a bio-impedance measurement device with a conventional structure.
Figure 1:
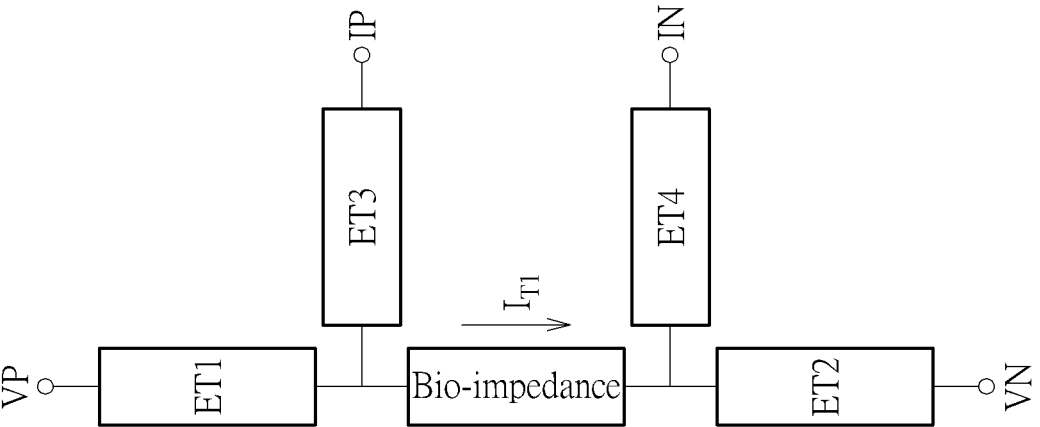

Please refer to FIG. 1. FIG. 1 is a schematic diagram of a conventional bio-impedance measurement device 1. The bio-impedance measurement device 1 may input a probing signal into a bio-impedance, receive a response signal related to the probing signal from the bio-impedance, and analyze the response signal to determine a bio-impedance value of the bio-impedance. The bio-impedance measurement device 1 includes a signal generator 10, a demodulation circuit 12 and a processor 14. The signal generator 10 is configured to generate the probing signal $I_{T1}$, and input the probing signal $I_{T1}$ into the bio-impedance through electrodes ET1, ET2. The demodulation circuit 12 is configured to receive the response signal $V_{B1}$ related to the probing signal $I_{T1}$ from the bio-impedance through electrodes ET3, ET4, and generate an in-phase signal $V_{I1}$ and a quadrature-phase signal $V_{Q1}$ according to the response signal $V_{B1}$. The processor 14 is coupled to the demodulation circuit 12, and configured to analyze the probing signal $I_{T1}$, the in-phase signal $V_{I1}$ and the quadrature-phase signal Voi to determine a bio-impedance value $Z_{meas}$ of the bio-impedance.

Figure 2:
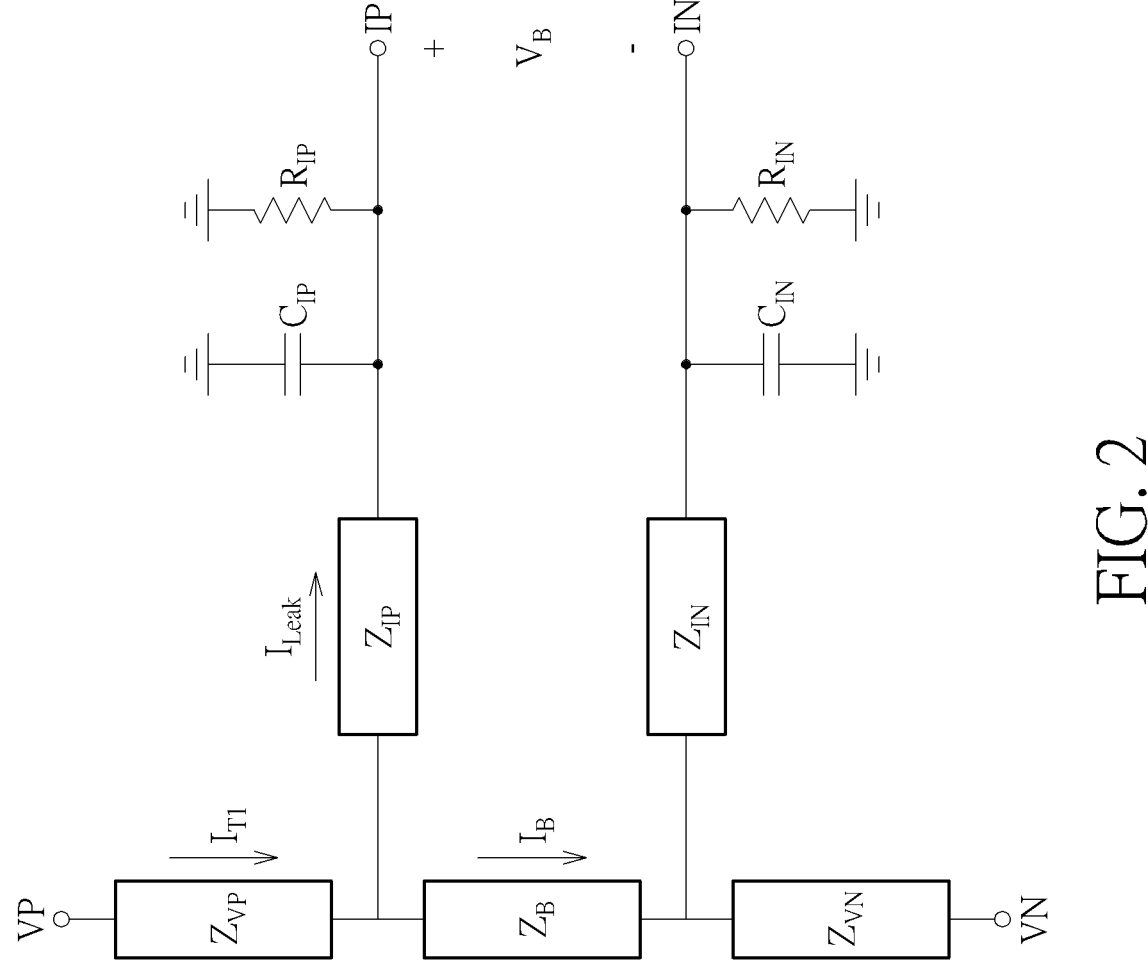
FIG. 2 is a schematic diagram illustrating a model of the configuration of the electrodes and the demodulation circuit.

It should be noted that the configuration of the electrodes and the demodulation circuit 12 may affect the measurement accuracy of the bio-impedance device 1. Please refer to FIG. 2. FIG. 2 is a model of the configuration of the electrodes ET1, ET2, ET3, ET4 and the demodulation circuit 12. The impedances $Z_B, Z_{VP}, Z_{VN}, Z_{IP}, Z_{IN}$ respectively represent the equivalent models of the bio-impedance and the electrodes ET1, ET2, ET3, ET4. The capacitance $C_{IP}, C_{IN}$ and the resistance $R_{IP}, R_{IN}$ respectively represent the parasitic capacitances and the parasitic resistances between the electrodes ET3, ET4 and the demodulation circuit 12. It should be noted that the capacitance $C_{IP}, C_{IN}$ and the resistance $R_{IP}, R_{IN}$ may include the parasitic capacitances and the parasitic resistances of the wiring between the electrodes ET3, ET4 and the demodulation circuit 12 and the parasitic capacitances and the parasitic resistances of the input end of the demodulation circuit 12, but not limited thereto. As shown in FIG. 2, the probing signal $I_{T1}$ input from the signal generator 10 flow to the bio-impedance and the electrodes respectively, that is, the probing current $I_B$ and the leakage current $I_{Leak}$. The leakage current $I_{Leak}$ may cause the bio-impedance value $Z_{meas}$ measured by the bio-impedance device 1 to deviate from the actual bio-impedance value $Z_B$ of the bio-impedance. In an embodiment, the bio-impedance value $Z_{meas}$ may be expressed as the equation (1) and the measurement error between $Z_{meas}$ and Ze may be obtained from the equation (1):

$$Z_{meas} = \frac{\left(Z_{CIP}//R_{IP} + Z_{CIN}//R_{IN}\right) + Z_B}{Z_B + Z_{IP} + Z_{IN} + Z_{CIP}//R_{IP} + Z_{CIN}//R_{IN}} \tag{1}$$

where $Z_{meas}$ represents the bio-impedance value measured by the bio-impedance device 1, $Z_B$ represents the actual bio-impedance value of the bio-impedance, $Z_{IP}, Z_{IN}$ respectively represent the impedances of the electrodes ET3, ET4, and $Z_{CIP}, Z_{CIN}, R_{IP}, R_{IN}$ respectively represent the impedances of the parasitic capacitances and the parasitic resistances between the electrodes ET3, ET4 and the demodulation circuit 12.

Specifically, the electrodes ET1, ET2, ET3, ET4 may be dry electrodes or wet electrodes. The typical model of the wet electrodes is 120 kΩ/36 nF, and the typical model of the dry electrodes is 500 kΩ/4.2 nF. In addition, the model for the dry electrodes in extreme dry and cold environments is 2.4 MΩ/0.3 nF. In the scenario of using the above three electrodes, the dry electrode in extreme dry and cold environments has the greatest impact on the measurement error.

Figure 3:
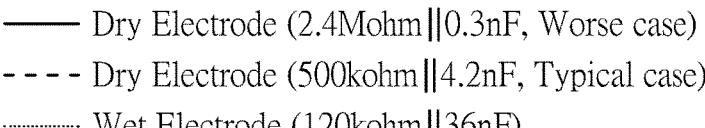
FIG. 3 is a schematic diagram illustrating a relationship between the parasitic capacitances of the electrodes and the measurement error.
Figure 3:
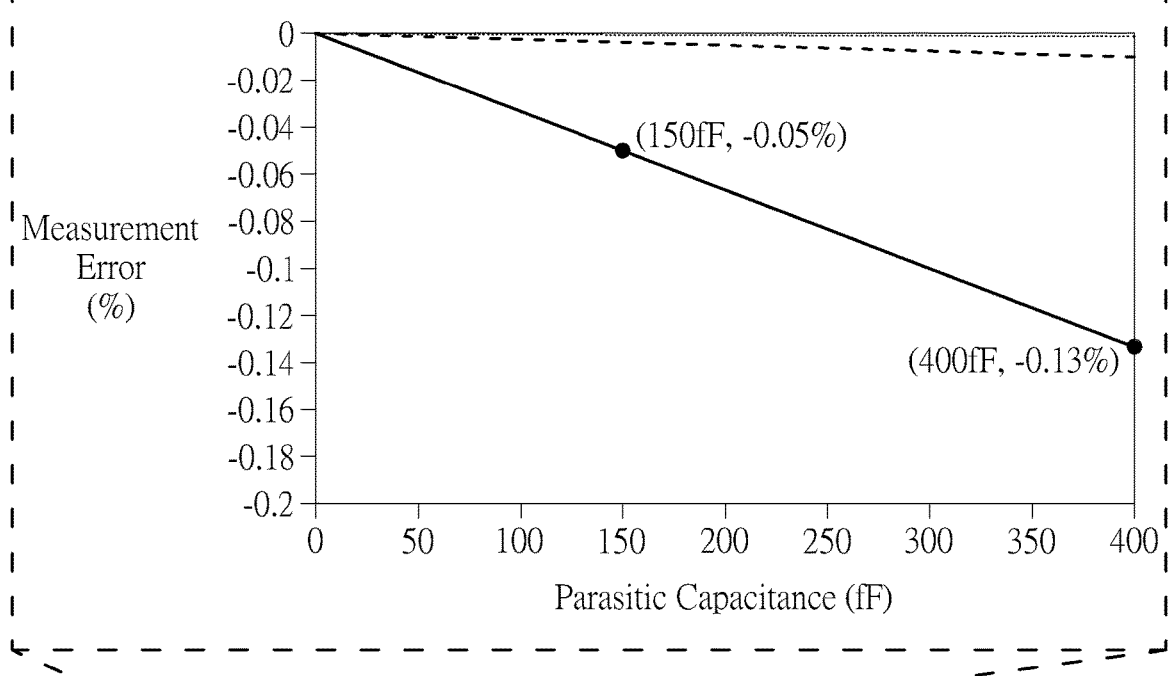
Figure 3:
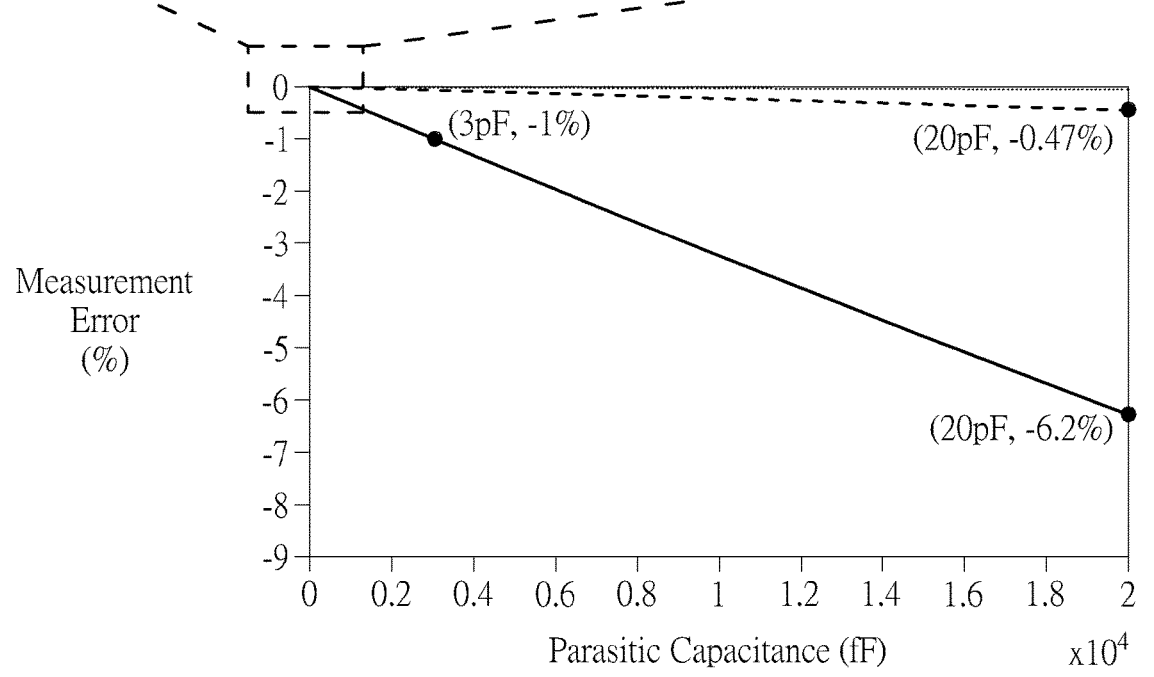

Please refer to FIG. 3. FIG. 3 illustrates the relationship between the parasitic capacitance $C_{IP}, C_{IN}$ of the electrodes and the measurement error. As shown in FIG. 3, when the parasitic capacitance $C_{IP}, C_{IN}$ is 20 pF, the measurement error related to the wet electrode is less than 0.05%, the measurement error related to the typical dry electrode is 0.47%, and the measurement error related to the dry electrode in extreme dry and cold environments is 6.2%. In addition, no matter which electrode is used, the measurement error will become larger as the parasitic capacitance increases.

Figure 4:
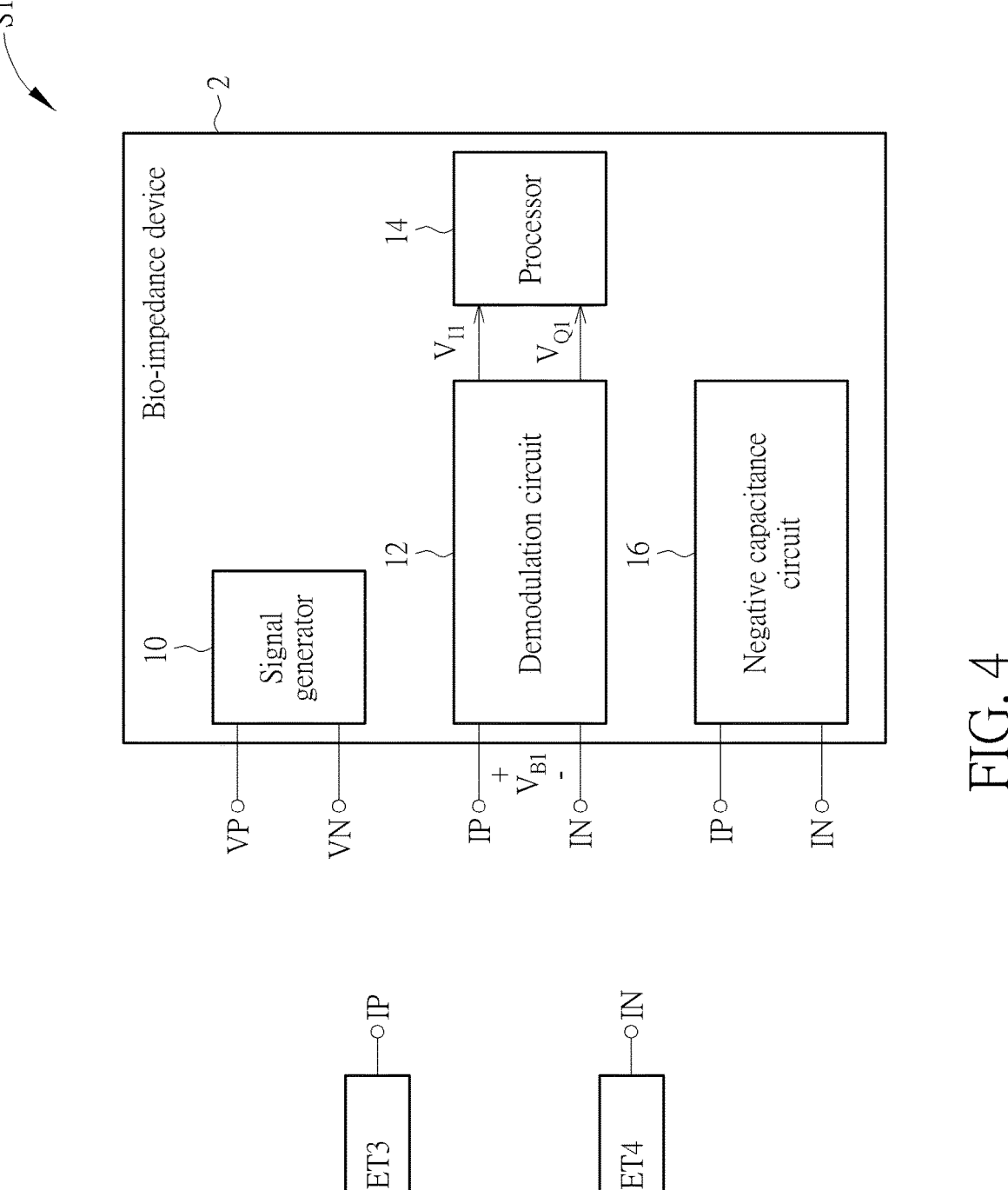
FIG. 4 is a schematic diagram of a bio-impedance measurement system according to an embodiment of the present invention.
Figure 5:
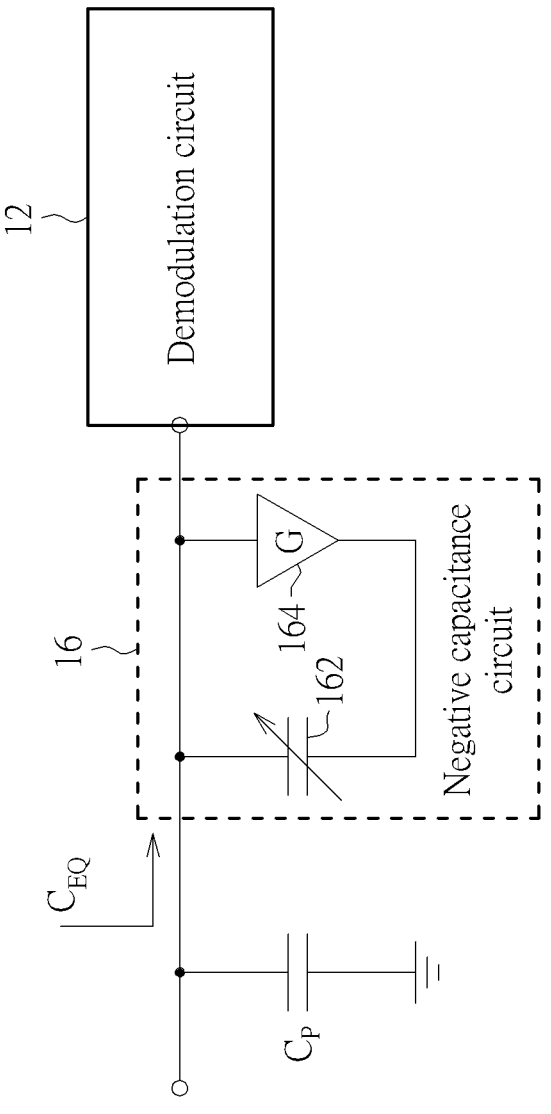
FIG. 5 is a schematic diagram illustrating a model of the negative capacitance circuit.

In order to reduce the measurement error caused by the parasitic capacitance, the present invention provides a bio-impedance measurement system S1 including the bio-impedance measurement device 2, a negative capacitance circuit 16 and the bio-impedance, and utilizes the probing signal to measure the bio-impedance value of the bio-impedance. Please refer to FIG. 4. FIG. 4 is a schematic diagram of the bio-impedance measurement system S1 according to an embodiment of the present invention. The bio-impedance measurement device 2 is derived from the bio-impedance measurement device 1, so the same elements are represented by the same symbols. As shown in FIG. 4, the negative capacitance circuit 16 is added to cancel the parasitic capacitance $C_{IP}, C_{IN}$. Specifically, the negative capacitance circuit 16 may be modeled as a first variable capacitor 162 and a first amplifier 164 as shown in FIG. 5. It should be noted that for the sake of simplicity, FIG. 5 only represents a single-ended model and assumes that the parasitic capacitance $C_{IP}, C_{IN}$ are equal to $C_P$. In an embodiment, the capacitance $C_{EQ}$ of the negative capacitance circuit 16 may be expressed as the equation (2):

$$C_{EQ} = -(G-1) \times C_{COMP1} \tag{2}$$

where $C_{EQ}$ represents the capacitance of the negative capacitance circuit 16, $C_{comp1}$ represents the capacitance of the first variable capacitor 162, and G represents the gain of the first amplifier 164.

The present invention may adjust the capacitance of the negative capacitance circuit to cancel the parasitic capacitance by appropriately selecting the capacitance $C_{comp1}$ and the gain G. That is, the sum of the capacitance $C_{EQ}$ and the parasitic capacitance $C_P$ is equal to zero.

Figure 6:
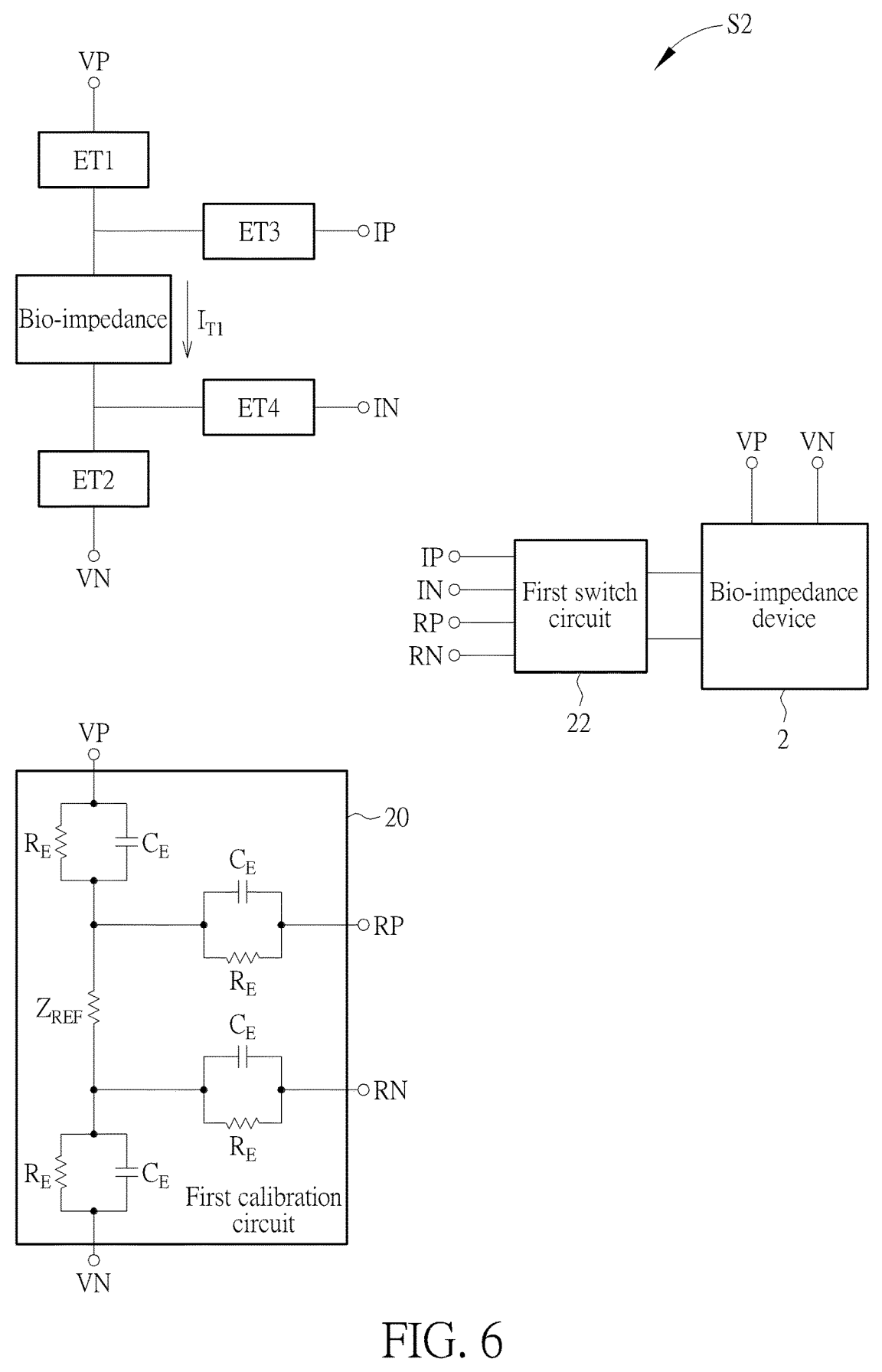

It should be noted that FIG. 4 is merely the embodiment of the present invention, and those skilled in the art may make appropriate adjustments according to the system requirements. For example, FIG. 6 is a schematic diagram of a bio-impedance measurement system S2 according to an embodiment of the present invention. The bio-impedance measurement system S2 is derived from the bio-impedance measurement system S1, so the same elements are represented by the same symbols. The difference between the bio-impedance measurement system S2 and the bio-impedance measurement system S1 is that a first switching circuit 22 is included between the bio-impedance measurement device 2 and the bio-impedance or a first calibration circuit 20. The first switching circuit 22 is configured to switch the bio-impedance measurement device 2 to receive the response signal from the bio-impedance or the first calibration circuit 20. As shown in FIG. 6, the first calibration circuit 20 is configured to adjust the capacitance $C_{EQ}$ of the negative capacitance circuit 16 and may be implemented with a reference impedance $Z_{REF}$ and four groups of resistor $R_E$ and capacitor $C_E$ connected in parallel. Each group of the resistor $R_E$ and the capacitor $C_E$ is configured to be as a replica circuit for each electrode. Specifically, the signal generator 10 is configured to generate the probing signal $I_{T1}$ and input the probing signal $I_{T1}$ into the reference impedance $Z_{REF}$ and the replica circuit of electrodes ET1 and ET2. The demodulation circuit 12 is configured to receive a reference response signal related to the probing signal $I_{T1}$ from the reference impedance through $Z_{REF}$ through the replica circuit of the electrodes ET3, ET4, and generate an in-phase signal $V_{I2}$ and a quadrature-phase signal $V_{Q2}$ according to the reference response signal. The processor 14 is coupled to the demodulation circuit 12, and configured to analyze the probing signal $I_{T1}$, the in-phase signal $V_{I2}$ and the quadrature-phase signal $V_{Q2}$ to determine a reference impedance value $Z_{meas\_R}$ of the reference impedance $Z_{REF}$. It should be noted that the bio-impedance measurement device 2 or the processor 14 may further include a memory to store an actual reference impedance value of the reference impedance and the reference impedance value $Z_{meas\_R}$ of the reference impedance. Since the configurations of measuring the reference impedance $Z_{REF}$ and measuring the bio-impedance are exactly the same and the reference impedance $Z_{REF}$ is independent of the process variations, the actual reference impedance value and the reference impedance value $Z_{meas\_R}$ of the reference impedance $Z_{REF}$ may be used to calibrate the measurement result of the bio-impedance by adjusting the capacitance $C_{EQ}$ of the negative capacitance circuit 16. In this way, the measurement error of the bio-impedance measurement device 2 in measuring the bio-impedance value may be reduced as the influence of the parasitic capacitance $C_{IP}$, $C_{IN}$ is reduced (e.g. the sum of the capacitance $C_{EQ}$ and the parasitic capacitance $C_P$ is adjusted to be equal to zero). It should be noted that the calibration principle is well known in the art, so it is not reiterated.

In an embodiment, the replica circuit of the dry electrode in extreme dry and cold environments may include the resistor $R_E$ of 2.4 MΩ and the capacitor $C_E$ of 0.3 nF. However, the resistor $R_E$ of 2.4 MΩ and the capacitor $C_E$ of 0.3 nF are only suitable for implementation on the circuit board and not within the chip. Therefore, the present invention further provides a bio-impedance measurement device 3 including a second calibration circuit 30. The difference between the bio-impedance measurement device 3 and the bio-impedance measurement device 2 or the bio-impedance measurement system S2 is that the second calibration circuit 30 may be implemented within the chip. The bio-impedance measurement device 3 is derived from the bio-impedance measurement device 2, so the same elements are represented by the same symbols. As shown in FIG. 7, the second calibration circuit 30 is added to dynamically adjust the negative capacitance circuit 16 to cancel the parasitic capacitance $C_{IP}$, $C_{IN}$.

Figure 8:
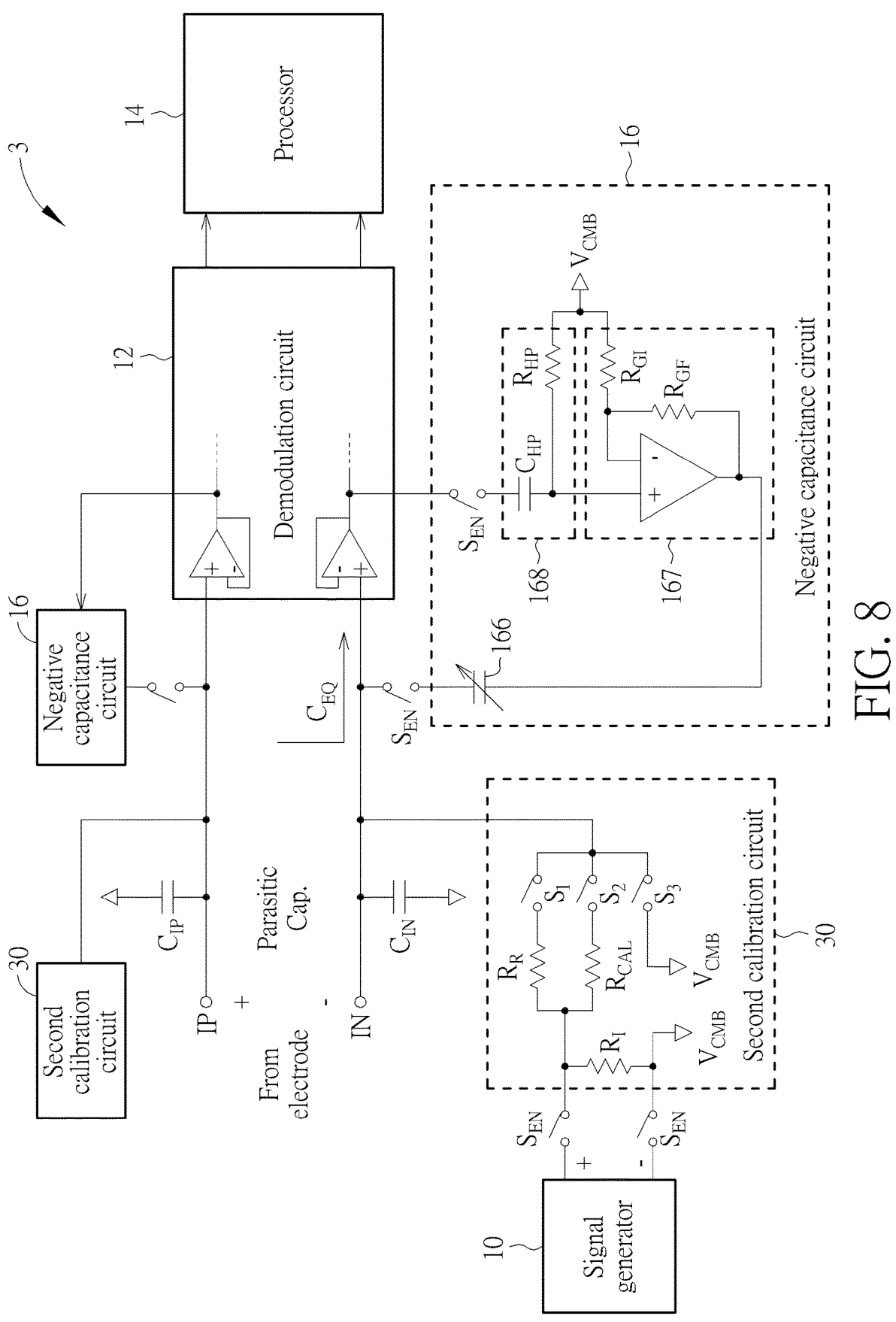
FIG. 8 is a detailed schematic diagram of the second calibration circuit and the negative capacitance circuit of the bio-impedance measurement device according to an embodiment of the present invention.
Figure 9:
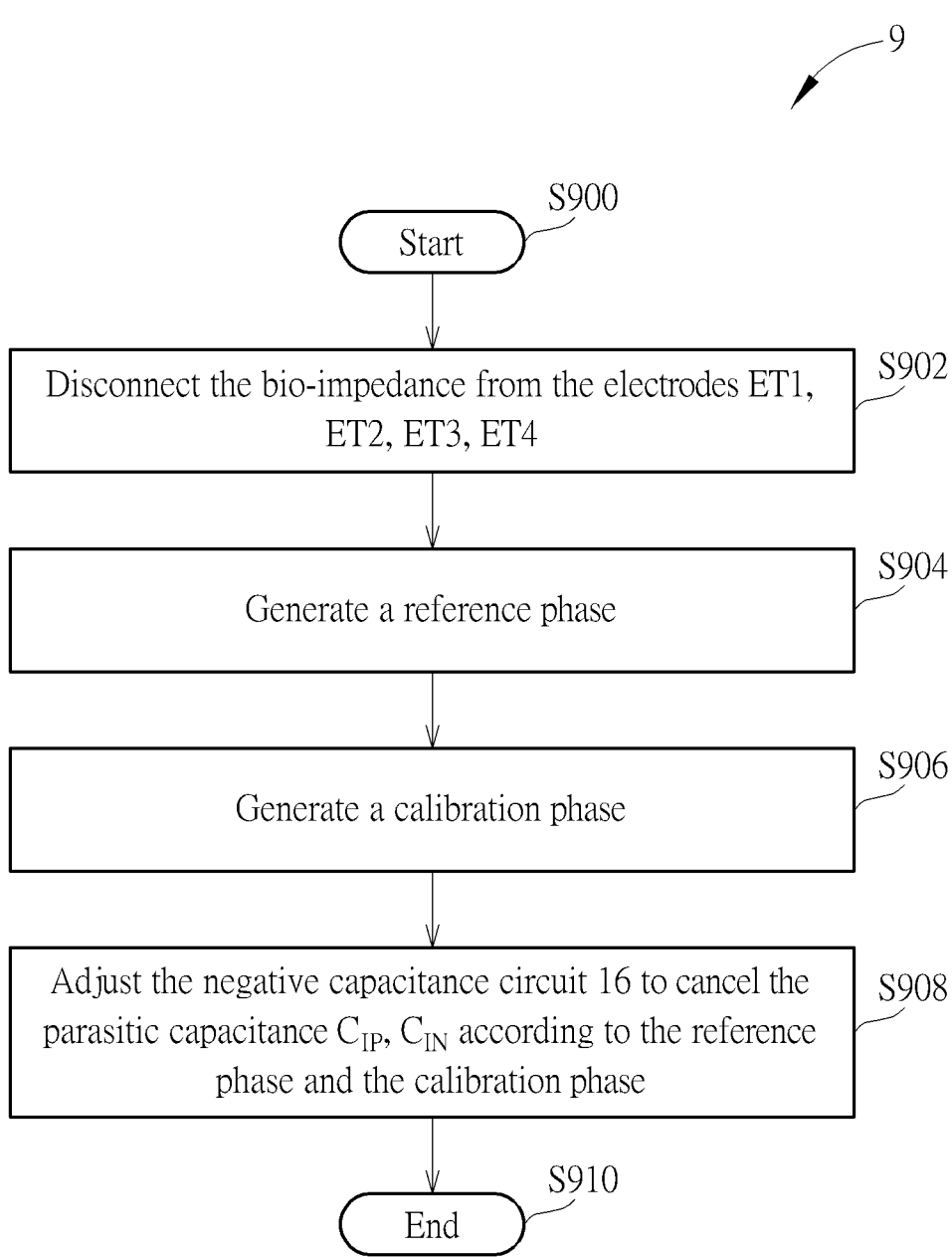
FIG. 9 is a flowchart of a parasitic capacitance cancellation method according to an embodiment of the present invention.

It should be noted that the bio-impedance measurement device 3 is the embodiment of the present invention, those skilled in the art may make different modifications accordingly, and is not limited thereto. For example, FIG. 8 is a detailed schematic diagram of the second calibration circuit 30 and the negative capacitance circuit 16 of the bio-impedance measurement device 3 according to an embodiment of the present invention. The negative capacitance circuit 16 includes a second variable capacitor 166, a second amplifier 167 and a high-pass filter 168. It should be noted that the operation principles of the second amplifier 167 and the high-pass filter 168 are well known in the art, so it is not reiterated. The second calibration circuit 30 includes an excitation resistor $R_I$, a reference resistor $R_R$, a calibration resistor $R_{CAL}$, and switches $S_1$, $S_2$, $S_3$. It should be noted that the input positive end IP of the demodulation circuit 12 is coupled to a group of the negative capacitance circuit 16 and the second calibration circuit 30, and the input negative end IN is coupled to another duplicated group of the negative capacitance circuit 16 and the second calibration circuit 30. It should be noted that the bio-impedance measurement device 3 or the processor 14 may further include a controller to execute a parasitic capacitance cancellation method to control the second calibration circuit 30 and to adjust the negative capacitance circuit 16 to cancel the parasitic capacitance $C_{IP}$, $C_{IN}$. The parasitic capacitance cancellation method may be summarized as a process 9, as shown in FIG. 9. The process 9 includes the following steps:

Step S900: Start.

Step S902: Disconnect the bio-impedance from the electrodes ET1, ET2, ET3, ET4.

Step S904: Generate a reference phase.

Step S906: Generate a calibration phase.

Step S908: Adjust the negative capacitance circuit 16 to cancel the parasitic capacitance $C_{IP}$, $C_{IN}$ according to the reference phase and the calibration phase.

Step S910: End.

According to the process 9, in step S902, before calibrating the parasitic capacitance $C_{IP}$, $C_{IN}$, the controller disconnects the electrodes from the bio-impedance and turns on switches $S_{EN}$; that is, the positive input end IP and the negative input end IN of the demodulation circuit 12 is coupled to the negative capacitance circuit 16, and the signal generator 10 is coupled to the second calibration circuit 30.

Figure 10A:
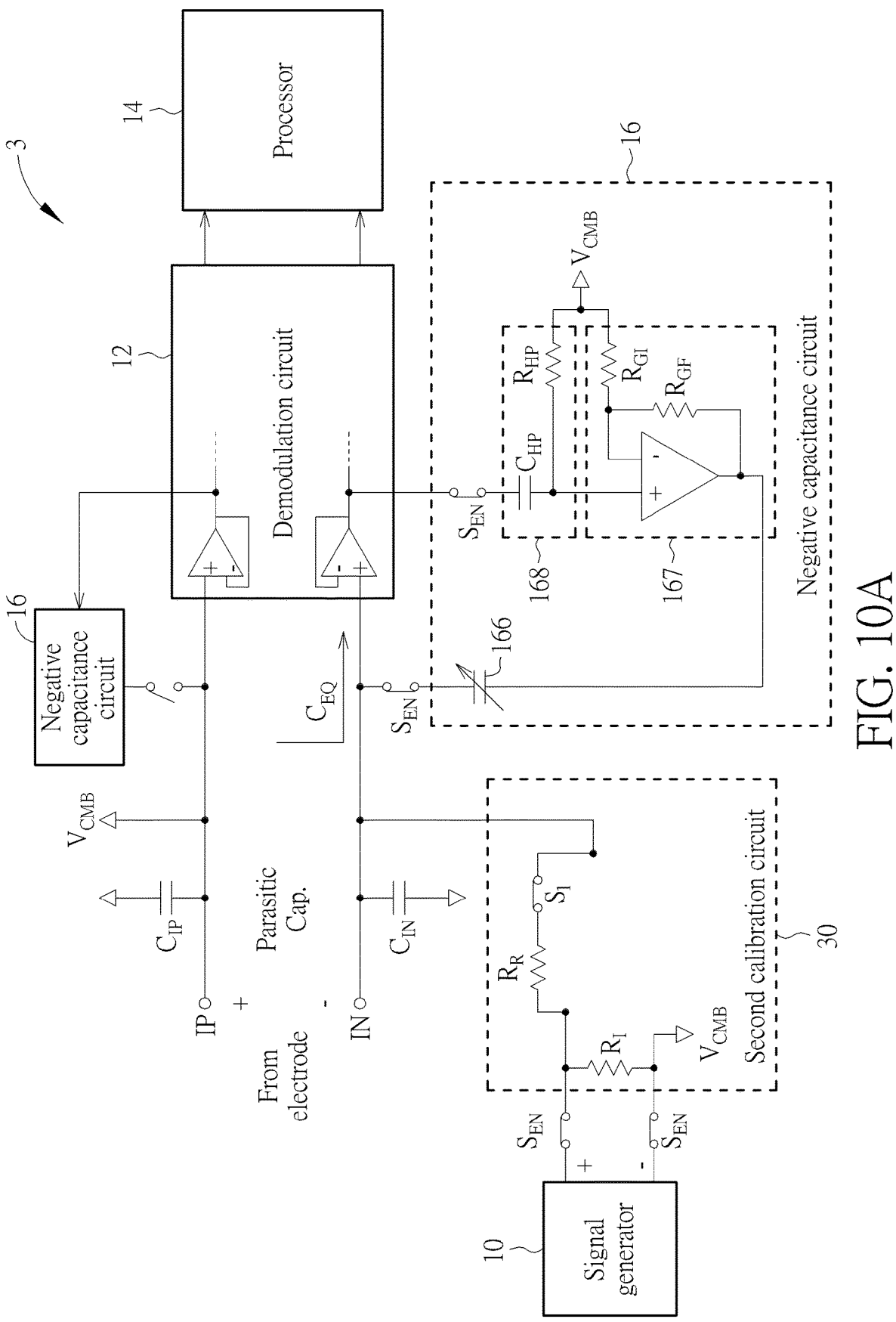
FIG. 10A is the detailed schematic diagram of the second calibration circuit and the negative capacitance circuit of the bio-impedance measurement device according to an embodiment of the present invention.

In step S904, the controller sets the switches $S_1$, $S_2$, $S_3$ in the second calibration circuit 30 coupled to the positive end IN of the demodulation circuit 12 to be on, off and off respectively, as shown in FIG. 10A. On the other hand, the controller sets the switch $S_3$ in the second calibration circuit 30 coupled to the negative end IP of the demodulation circuit 12 to be on; that is, the negative end of the demodulation circuit 12 is coupled to the common mode voltage source $V_{CMB}$. In addition, the controller sets the capacitance $C_{comp2}$ of the second variable capacitor 166 to 0. Specifically, the signal generator 10 generates the probing signal $I_{T1}$ and inputs the probing signal $I_{T1}$ into the second calibration circuit 30. The demodulation circuit 12 receives a first response signal $V_{exc1}$ related to the probing signal $I_{T1}$ from the excitation resistor $R_I$ and the reference resistor $R_R$. In an embodiment, the first response signal $V_{exc1}$ may be expressed as the equation (1):

$$V_{EXC1} = \frac{I_{T1} \times R_I}{1 + sC_{IN}(R_I + R_R)} \qquad (1)$$

where $V_{exc1}$ represents the first response signal, $I_{T1}$ represents the probing signal, $C_{IN}$ represents the parasitic capacitance of the positive input end of the demodulation circuit 12, $R_I$ represents the excitation resistor and $R_R$ represents the reference resistor.

The demodulation circuit 12 generates an in-phase signal $V_{I\_exc1}$ and a quadrature-phase signal $V_{Q\_exc1}$ according to the first response signal $V_{exc1}$. The processor 18 analyzes the probing signal $I_{T1}$, the in-phase signal $V_{I\_exc1}$ and the quadrature-phase signal $V_{Q\_exc1}$ to determine the reference phase $Phase_{REF}$. In an embodiment, the reference phase $Phase_{REF}$ may be expressed as the equation (2):

$$Phase_{REF} = -\omega C_{IN}(R_I + R_R) \qquad (2)$$

where $Phase_{REF}$ represents the reference phase, $C_{IN}$ represents the parasitic capacitance of the positive input end of the demodulation circuit 12, $R_I$ represents the excitation resistor and $R_R$ represents the reference resistor.

Figure 10B:
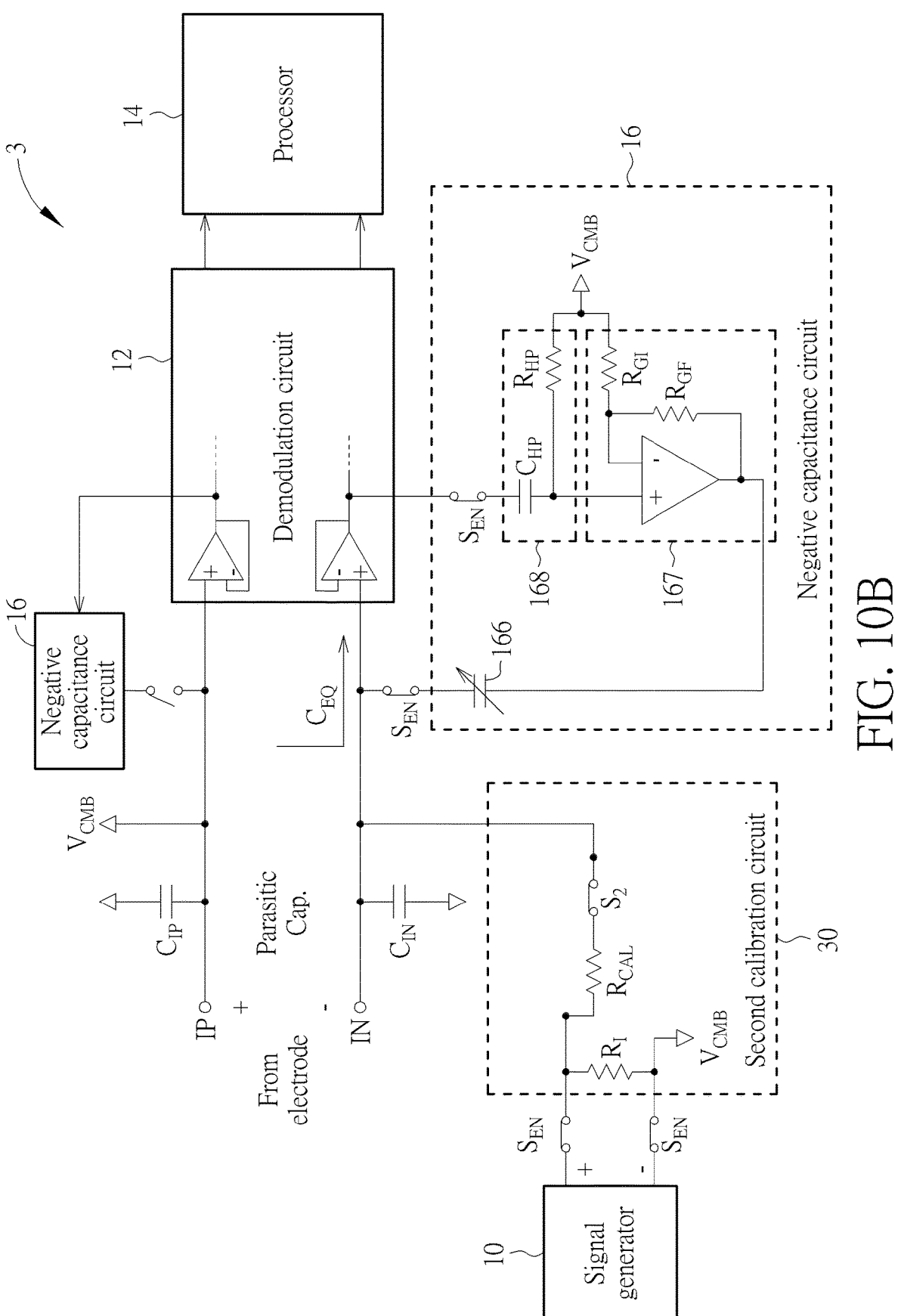
FIG. 10B is the detailed schematic diagram of the second calibration circuit and the negative capacitance circuit of the bio-impedance measurement device according to an embodiment of the present invention.

In step S906, the controller sets the switches $S_1$, $S_2$, $S_3$ in the second calibration circuit 30 coupled to the positive end of the demodulation circuit 12 to be off, on and off respectively, as shown in FIG. 10B. On the other hand, the controller sets the switch $S_3$ in the second calibration circuit 30 coupled to the negative end of the demodulation circuit 12 to be on, that is, the negative end of the demodulation circuit 12 is coupled to the common mode voltage source $V_{CMB}$. Specifically, the signal generator 10 generates the probing signal $I_{T1}$ and inputs the probing signal $I_{T1}$ into the second calibration circuit 30. The demodulation circuit 12 receives a second response signal $V_{exc2}$ related to the probing signal $I_{T1}$ from the excitation resistor $R_I$ and the calibration resistor $R_{CAL}$. In an embodiment, the second response signal $V_{exc2}$ may be expressed as the equation (3):

$$V_{EXC2} = \frac{I_{T1} \times R_I}{1 + s(C_{IN} + C_{EQ})(R_I + R_{CAL})} \tag{3}$$

where $V_{exc2}$ represents the second response signal, $I_{T1}$ represents the probing signal, $C_{IN}$ represents the parasitic capacitance of the positive input end of the demodulation circuit 12, $C_{EQ}$ represents the capacitance of the negative capacitance circuit 16 coupled to the positive input end of the demodulation circuit 12, $R_I$ represents the excitation resistor and $R_{CAL}$ represents calibration resistor.

The demodulation circuit 12 generates an in-phase signal $V_{I\_exc2}$ and a quadrature-phase signal $V_{Q\_exc2}$ according to the second response signal $V_{exc2}$. The processor 18 analyzes the probing signal $I_{T1}$, the in-phase signal $V_{I\_exc2}$ and the quadrature-phase signal $V_{Q\_exc2}$ to determine the calibration phase $Phase_{CAL}$. In an embodiment, the calibration phase $Phase_{CAL}$ may be expressed as the equation (4):

$$Phase_{CAL} = -\omega(C_{IN} + C_{EQ})(R_I + R_{CAL}) \tag{4}$$

where $Phase_{REF}$ represents the reference phase, $C_{IN}$ represents the parasitic capacitance of the positive input end of the demodulation circuit 12, $C_{EQ}$ represents the capacitance of the negative capacitance circuit 16 coupled to the positive input end of the demodulation circuit 12, $R_I$ represents the excitation resistor, $R_R$ represents the reference resistor and $R_{CAL}$ represents calibration resistor.

It should be noted that the design principle of the negative capacitance circuit 16 and the second amplifier 167 should be well known in the art, so it is not reiterated here. In an embodiment, the capacitance $C_{EQ}$ of the negative capacitance circuit 16 in the equations (3), (4) may be expressed as the equation (5) and the equation (6):

$$G = 1 + \frac{R_{GF}}{R_{GI}} \tag{5}$$

$$C_{EQ} = -(G - 1) \times C_{comp2} \tag{6}$$

where G represents the gain of the second amplifier 167, $C_{comp2}$ represents the capacitance of the second variable capacitor 166, $C_{EQ}$ represents the capacitance of the negative capacitance circuit 16 coupled to the positive input end of the demodulation circuit 12.

In step S908, the controller adjusts the capacitance $C_{comp2}$ of the second variable capacitor 166 until the reference phase $Phase_{REF}$ and the calibration phase $Phase_{CAL}$ are equal. The capacitance $C_{comp2}$ in this situation of the second variable capacitor 166 may be used to cancel parasitic capacitance $C_{IN}$. In an embodiment, the sum of the capacitance $C_{EQ}$ and the parasitic capacitance $C_{IN}$ may be expressed as the equation (7):

$$C_{IN} + C_{EQ} = C_{IN} \times \frac{R_I + R_R}{R_I + R_{CAL}} \tag{7}$$

where $C_{IN}$ represents the parasitic capacitance of the positive input end of the demodulation circuit 12, $C_{EQ}$ represents the capacitance of the negative capacitance circuit 16 coupled to the positive input end of the demodulation circuit 12, $R_I$ represents the excitation resistor, $R_R$ represents the reference resistor and $R_{CAL}$ represents the calibration resistor.

In an embodiment, the present invention selects the excitation resistor $R_I$ to be 2 kΩ, the reference resistor $R_R$ to be 2 kΩ, and the calibration resistor $R_{CAL}$ to be 400 kΩ. The equation (7) may be simplified to the equation (8):

$$C_{IN} + C_{EQ} = C_{IN} \times \frac{2 + 2}{2 + 400} \tag{8}$$

where $C_{IN}$ represents the parasitic capacitance of the positive input end of the demodulation circuit 12, $C_{EQ}$ represents the capacitance of the negative capacitance circuit 16 coupled to the positive input end of the demodulation circuit 12.

According to the equation (8), the sum of the capacitance $C_{EQ}$ and the parasitic capacitance $C_{IN}$ is approximately equal to one hundredth of the parasitic capacitance $C_{IN}$. In other words, the parasitic capacitance of the positive input end of the demodulation circuit 12 is reduced from $C_{IN}$ to $C_{IN}/100$. On the other hand, the controller may further execute the steps S904-S908 to reduce the parasitic capacitance of the negative input end of the demodulation circuit 12 is reduced from $C_{IP}$ to $C_{IP}/100$. The detail description and derivative changes of the parasitic capacitance cancellation method for the negative input end of the demodulation circuit 16 are described as above, and will not be reiterated.

In short, by appropriately selecting the capacitance $C_{comp2}$ and a ratio of the resistances of the excitation resistor $R_I$, the reference resistor $R_R$ and the resistance of the calibration resistor $R_{CAL}$ to be greater than a threshold, for example, the threshold is equal to 100, the present invention may effectively reduce the parasitic capacitance at the input end of the demodulation circuit 16 and thereby reduce the measurement error.

Figure 11:
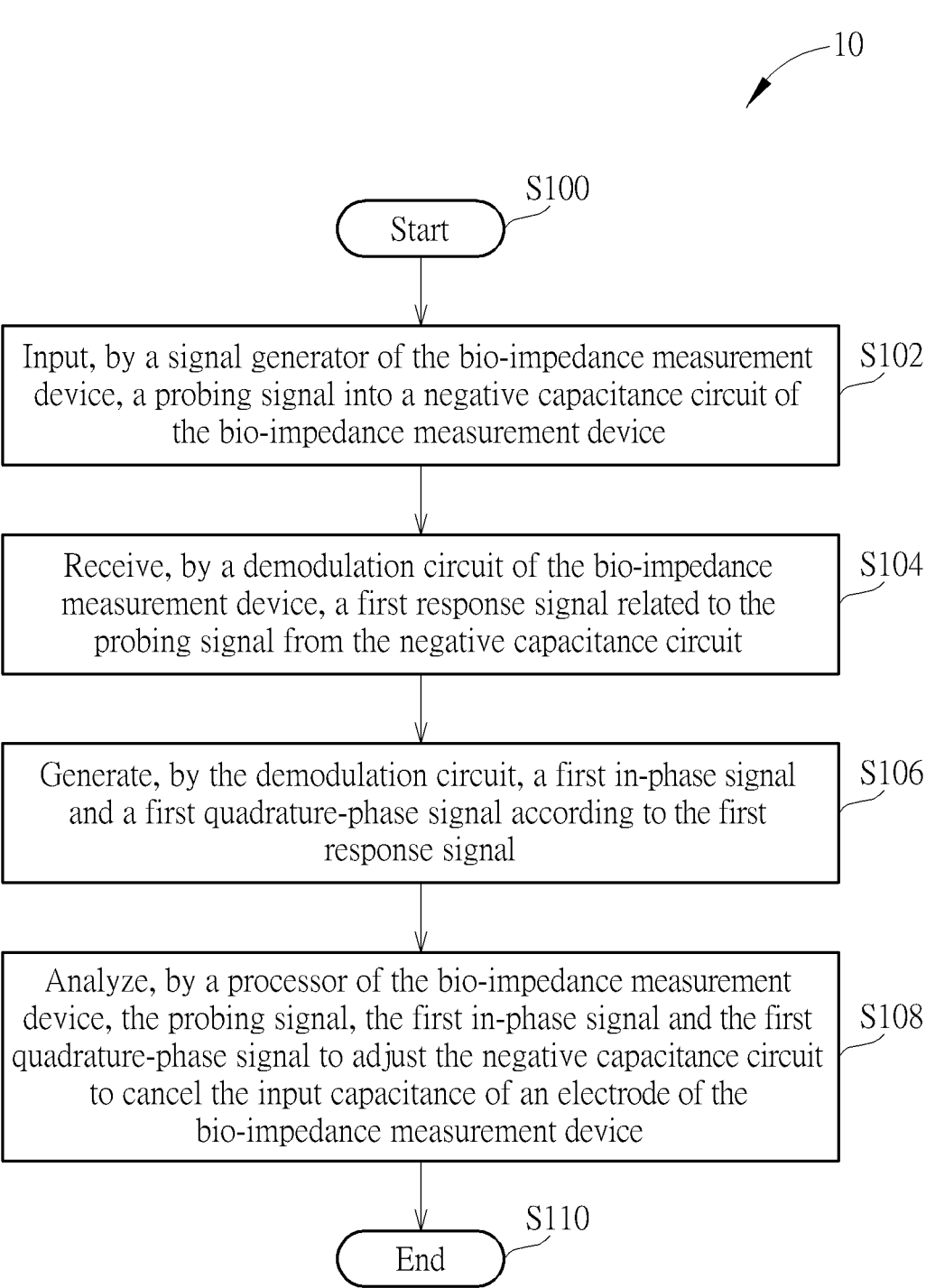
FIG. 11 is a flowchart of a bio-impedance measurement method according to an embodiment of the present invention.

The operations of the bio-impedance measurement devices 2-3 may be summarized as a bio-impedance measurement method 10, as shown in FIG. 11. The bio-impedance measurement method 10 includes the following steps:

Step S100: Start.

Step S102: Input, by a signal generator of the bio-impedance measurement device, a probing signal into a negative capacitance circuit of the bio-impedance measurement device.

Step S104: Receive, by a demodulation circuit of the bio-impedance measurement device, a first response signal related to the probing signal from the negative capacitance circuit.

Step S106: Generate, by the demodulation circuit, a first in-phase signal and a first quadrature-phase signal according to the first response signal.

Step S108: Analyze, by a processor of the bio-impedance measurement device, the probing signal, the first in-phase signal and the first quadrature-phase signal to adjust the negative capacitance circuit to cancel the input capacitance of an electrode of the bio-impedance measurement device.

Step S110: End.

The detail description and derivative changes of the bio-impedance measurement method 5 are described as above, and will not be reiterated.

It should be noted that the bio-impedance measurement devices 2-3 are different embodiments of the present invention. Those skilled in the art should readily make combinations, modifications and/or alterations on the abovementioned description and examples. The abovementioned description, steps, procedures and/or processes including suggested steps can be realized by means that could be hardware, software, firmware (known as a combination of a hardware device and computer instructions and data that reside as read-only software on the hardware device), an electronic system, or combination thereof. Examples of hardware can include analog, digital and mixed circuits known as microcircuit, microchip, or silicon chip. Examples of the electronic system may include a system on chip (SoC), system in package (SiP), a computer on module (COM) and the computer system. Any of the abovementioned procedures and examples above may be compiled into program codes or instructions that are stored in the memory. The memory may include read-only memory (ROM), flash memory, random access memory (RAM), subscriber identity module (SIM), hard disk, or CD-ROM/DVD-ROM/BD-ROM, but not limited thereto. The processor 18 may read and execute the program codes or the instructions stored in the memory for realizing the abovementioned functions.

In summary, the bio-impedance measurement device and the bio-impedance measurement method of the present invention utilize a negative capacitance circuit to cancel the parasitic capacitance of the input end of the demodulation circuit. In this way, compared with the prior art, the measurement errors of the bio-impedance measurement device may be significantly reduced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A bio-impedance measurement device, for measuring a bio-impedance, comprising:

an electrode;

a negative capacitance circuit, coupled to the electrode;

a signal generator, configured to input a probing signal into the negative capacitance circuit;

a demodulation circuit, coupled to the electrode and the negative capacitance circuit, configured to receive a first response signal related to the probing signal from the negative capacitance circuit and generate a first in-phase signal and a first quadrature-phase signal according to the first response signal, wherein the demodulation circuit and the electrode comprise an input capacitance; and a processor, coupled to the negative capacitance circuit and the demodulation circuit, configured to adjust the negative capacitance circuit to cancel the input capacitance according to the first in-phase signal and the first quadrature-phase signal.

2. The bio-impedance measurement device of claim 1, wherein the negative capacitance circuit comprises:

a variable capacitor; and an amplifier;

wherein a first end of the variable capacitor and an input end of the amplifier are coupled to the electrode and the demodulation circuit, and a second end of the variable capacitor is coupled to an output end of the amplifier;

wherein the processor adjusts capacitance of the variable capacitor to cancel the input capacitance according to the first in-phase signal and the first quadrature-phase signal.

3. The bio-impedance measurement device of claim 2, wherein the negative capacitance circuit further comprises:

a calibration circuit, coupled to the electrode and the demodulation circuit, comprising a first resistor, a second resistor and a switching circuit, wherein the switching circuit is configured to select the calibration circuit to receive the probing signal through the first resistor or the second resistor, wherein the first response signal is related to the probing signal received through the first resistor; and wherein the processor further controls the calibration circuit to receive the probing signal through the second resistor and adjusts the capacitance of the variable capacitor as 0; the demodulation circuit is further configured to receive a second response signal related to the probing signal from the negative capacitance circuit and generate a second in-phase signal and a second quadrature-phase signal according to the second response signal;

and the processor adjusts the negative capacitance circuit to cancel the input capacitance according to the first in-phase signal, the first quadrature-phase signal, the second in-phase signal and the second quadrature-phase signal.

4. The bio-impedance measurement device of claim 3, wherein a ratio of a resistance of the second resistor to that of the first resistor is greater than a threshold.

5. A bio-impedance measurement method, for a bio-impedance measurement device, comprising:

inputting, by a signal generator of the bio-impedance measurement device, a probing signal into a negative capacitance circuit of the bio-impedance measurement device;

receiving, by a demodulation circuit of the bio-impedance measurement device, a first response signal related to the probing signal from the negative capacitance circuit;

generating, by the demodulation circuit, a first in-phase signal and a first quadrature-phase signal according to the first response signal; and analyzing, by a processor of the bio-impedance measurement device, the probing signal, the first in-phase signal and the first quadrature-phase signal to adjust the negative capacitance circuit to cancel an input capacitance between the demodulation circuit and an electrode of the bio-impedance measurement device.

6. The bio-impedance measurement method of claim 5, wherein the negative capacitance circuit comprises:

a variable capacitor; and an amplifier;

wherein a first end of the variable capacitor and an input end of the amplifier are coupled to the electrode and the demodulation circuit, and a second end of the variable capacitor is coupled to an output end of the amplifier;

wherein the processor adjusts capacitance of the variable capacitor to cancel the input capacitance according to the first in-phase signal and the first quadrature-phase signal.

7. The bio-impedance measurement method of claim 6, wherein the negative capacitance circuit further comprises:

a calibration circuit, coupled to the electrode and the demodulation circuit, comprising a first resistor, a second resistor and a switching circuit, wherein the switching circuit is configured to select the calibration circuit to receive the probing signal through the first resistor or the second resistor, wherein the first response signal is related to the probing signal received through the first resistor; and wherein the processor further controls the calibration circuit to receive the probing signal through the second resistor and adjusts the capacitance of the variable capacitor as 0; the demodulation circuit is further configured to receive a second response signal related to the probing signal from the negative capacitance circuit and generate a second in-phase signal and a second quadrature-phase signal according to the second response signal;

and the processor adjusts the negative capacitance circuit to cancel the input capacitance according to the first in-phase signal, the first quadrature-phase signal, the second in-phase signal and the second quadrature-phase signal.

8. The bio-impedance measurement method of claim 7, wherein a ratio of a resistance of the second resistor to that of the first resistor is greater than a threshold.

\* \* \* \* \*